United States Patent [19]
Handa et al.

[11] Patent Number: 5,580,880
[45] Date of Patent: Dec. 3, 1996

[54] METHOD FOR THE TREATMENT OF XEROSTOMIA

[75] Inventors: Harumi Handa, Iruma; Yasuyoshi Takeshita, Utsunomiya, both of Japan

[73] Assignee: Snow Brand Milk Products Co., Ltd., Hokkaido, Japan

[21] Appl. No.: 466,373

[22] Filed: Jun. 6, 1995

[30] Foreign Application Priority Data

Jun. 27, 1994 [JP] Japan ................................. 6-168982

[51] Int. Cl.$^6$ .................................................. A61K 31/44
[52] U.S. Cl. .................................................. 514/305
[58] Field of Search ............................................. 514/305

[56] References Cited

U.S. PATENT DOCUMENTS

| | | | |
|---|---|---|---|
| 4,855,290 | 8/1989 | Fisher et al. | 514/278 |
| 4,906,455 | 3/1990 | Hoerman | 424/48 |
| 4,917,674 | 4/1990 | Molinoff | 604/286 |
| 4,983,378 | 1/1991 | Parnell | 424/48 |
| 4,997,654 | 3/1991 | Corsello et al. | 424/440 |
| 5,078,129 | 1/1992 | Kleinberg et al. | 128/200.14 |
| 5,340,821 | 8/1994 | Abe et al. | 514/305 |

FOREIGN PATENT DOCUMENTS

| | | |
|---|---|---|
| 0205247 | 12/1986 | European Pat. Off. . |
| 0303391 | 2/1989 | European Pat. Off. . |
| 0578511A1 | 1/1994 | European Pat. Off. . |

OTHER PUBLICATIONS

Y. Iwabuchi et al., "Salivary Secretion and Histopathological Effects after Single Administration of the Muscarinic Agonist SNI–2011 in MRL/lpr Mice", *Arch. int. Pharmacodyn.* 328:315–325 (1994).

Y. Iwabuchi et al., "Sialogogic Activities of SNI–2011 Compared with those of Pilocarpine and McN–A–343 in Rat Salivary Glands: Identification of a Potential Therapuetic Agent for Treatment of Sjorgen's Syndrome" *Gen. Pharmac.* 25(1):123–129 (1994).

Y. Ohtani et al., "Phase I Study of FKS–508–Single and Multiple Dose Studies" *European Journal of Pharmacology* 183:1038 (1990).

M. Navazesh; I. I. Ship; "Xerostomia: Diagnosis and Treatment", Am. Otolaryngol, 4, 283–292, (1983).

*Primary Examiner*—Raymond Henley, III
*Attorney, Agent, or Firm*—Testa, Hurwitz & Thibeault, LLP

[57] ABSTRACT

A method for the treatment of xerostomia not caused by Sjogren's syndrome comprising administering to an affected individual an effective amount of a derivative of spirooxathiolane-quinuclidine.

3 Claims, No Drawings

METHOD FOR THE TREATMENT OF XEROSTOMIA

FIELD OF THE INVENTION

The present invention relates to a therapeutic agent for the treatment of xerostomia not caused by Sjogren's syndrome, comprising a derivative of spirooxathiolane-quinuclidine or an acid addition salt thereof as an active ingredient.

BACKGROUND OF THE INVENTION

Stomatoxerosis is generally called "xerostomia" or "dry mouth" and its manifestation is characterized by decreased or deficient secretion of saliva caused by various factors. Since many factors are related to the secretion of saliva, it is very difficult to investigate the cause of xerostomia.

Considering the causes, it is known that various diseases which cause organic changes in salivary glands, lesions in salivary glands accompanied by systemic diseases, necrosis of salivary gland cells caused by radiotherapy, HIV infection, hypofunction of scretion caused by aging, the effect of various medicines and, further, mental fatigue or stress due to complex social life situations bring about these symptoms.

With age, stomatoxerosis is a common symptom, which is observed in 16% of males older than 70 years and 25% of females of the same age as above and are considered to be caused by a regressive change in salivary glands due to aging.

Further, there are many pharmaceutical drugs which cause hyposecretion of salivary glands, e.g., it has been reported that the number of such drugs is more than 100, and that the ratio of the patients complaining with dry mouth increased as the number of the species of drugs administered increased. For example, diuretics such as trichloromethiazide, furosemide, etc., antihypertensive such as reserpine, clonidine hydrochloride, etc., anticholines such as atropine sulfate, etc., antihistamines such as chlorpheniramine maleate, etc., various types of antitussives and expectorants, antiparkinsonism agents, psychotropic agents, antidepressants, tranquilizers, muscle relaxants, etc., are exemplified as drugs causing dry mouth.

In addition, while radiotherapy has been playing an important role for the treatment of malignant tumors in the field of stomatosurgery and otolaryngology, severe injury to salivary glands is inevitable due to a broad radiation area during the treatment, leading to severe xerostomia. The number of such patients as the above is anticipated to increase with the prevalence of radiotherapy.

Symptoms of xerostomia include not only intraoral dryness but also many and severe problems in daily life such as intraoral utrication, pain, glossalgia, dysgeusia, atrophy of papilla lingualis, inflammation of tunica mucosa oris, ulceration, rhagades of lingua orangulus oris, difficulties in mastication, somatic swallowing or conversation, etc.

Therefore, an appropriate countermeasure to the above is strongly required.

At present the methods of treatment of these symptoms include artificial saliva, mouth-wash, etc., but these have only a temporary wetting effect in the mouth. Alternatively, parotin, cepharanthin and various kinds of chinese medicines are used in practice, but have adverse effects or insufficient therapeutic effect. Thus, satisfactory therapeutic methods for xerostomia not caused by Sjogren's syndrome have not yet been established.

The object of the present invention is to synthesize chemical compounds to augment saliva secretion by stimulating exocrine glands, particularly, the muscarinic $M_3$ receptor; to provide a therapeutic agent for the treatment of xerostomia without systemic adverse effects and with the least toxicity and to alleviate pain in patients with dry mouth, based on recent developments in research on parasympathetic nervous system, that is, cholinergic receptors.

The present inventors have synthesized various compounds and investigated their efficacy to attain the above objects and found that a certain kind of derivative of spirooxathiolane-quinuclidine, or an acid addition salt thereof having a formula [I] exhibits an excellent effect and accomplished the present invention.

SUMMARY OF THE INVENTION

Accordingly, the present invention relates to a therapeutic agent for the treatment of xerosotmia not caused by Sjogren's syndrome, comprising a derivative of spirooxathiolane-quinuclidine or an acid addition salt thereof having a formula (I) as an active ingredient.

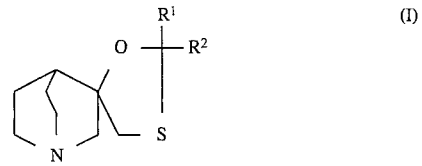

wherein $R^1$ and $R^2$ may be the same or different and each represents hydrogen, alkyl, cyclopentyl, cyclohexyl, aryl, diarylmethilol or alkyl which is substituted by one or more aryl groups.

DETAILED DESCRIPTION OF THE INVENTION AND PREFERRED EMBODIMENT

Alkyl groups of the compounds represented in the aforementioned formula (I) of the present invention can be methyl, ethyl, n-propyl, iso-propyl, butyl, sec buyl, tert-butyl, etc., and aryl groups can be phenyl and so on. These compounds are described in Japanese patent laid-open (kokai) No. 280,497/1986 and are known in the art.

The following compounds among these can be exemplified as derivatives of spirooxathiolane quinuclidine used in the present invention:
2-methylspiro(1,3-oxathiolane-5,3')quinuclidine
2-diphenylmethylspiro(1,3-oxathiolane-5,3')quinuclidine
2-methyl-2-phenylspiro(1,3-oxathiolane-5,3')quinuclidine These compounds of the present invention include geometrical isomers, enantiomers, diastereomers, racemates and any of these. In addition, acid addition salts thereof include either inorganic or organic acid addition salts, such as those of hydrochloric acid, sulfuric acid, phosphoric acid, sulfamic acid, lactic acid, succinic acid, maleic acid and so on.

Further, the derivatives of spirooxathiolane-quinuclidine of the present invention can be easily prepared by the methods described in the aforementioned Japanese patent laid-open (kokai) No. 280,497/1986, for example, by reacting 3-hydroxy-3-mercaptomethyl-quinuclidine with a carbonyl compound represented in a formula $R^1$—CO—$R^2$ ($R^1$-and-$R^2$ can be the same as the above), followed by isolation of the objective compound from the reaction mixture.

Isolation of an optical isomer or other isomer from these compounds can be carried out by the methods described in the above laid-open patent or in Japanese patent laid-open (kokai) No. 22,280/1990.

Among the derivatives of the present invention, 2-methylspiro (1,3-oxathiolane-5,3')quinuclidine hydrochloride represented in the following formula (II), especially, the cis-isomer, or a mixture of the cis-isomer and trans-isomer enriched with the cis-isomer, is preferred because of its higher therapeutic effect.

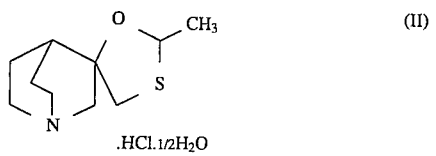

When the therapeutic agent for the treatment of xerostomia of the present invention is applied for curing disease, the compound represented in the aforementioned formula (I) is administered as an active ingredient singly, or combined with pharmaceutically acceptable carriers in a suitable dosage form of pharmaceutical composition for oral, parenteral, topical or rectal administration, e.g., capsules, tablets, powders, granules, injections, ointments, suppositories etc.

As pharmaceutical preparations suitable for oral administration, solid compositions such as capsules, tablets, powders, granules, or troches; and liquid compositions, such as syrups or suspensions, are exemplified.

These compositions for oral administration such as capsules, tablets and granules are prepared according to a usual methods in the art, using as vehicles, for example, starch, lactose, white sugar, mannitol, carboxymethylcellulose, corn starch, inorganic salts, etc. In addition to these vehicles, binders, disintegrators, surfactants, lubricants, fluidity accelerators, correctives, colorants, perfumes etc., may be used appropriately.

Specific examples are described as follows:

BINDERS

Starch, dextrin, gum arabic, gelatin, hydroxypropyl starch, methylcellulose, sodium carboxymethylcellulose, hydroxypropylcellulose, crystalline cellulose, ethylcellulose, polyvinyl pyrrolidone and Macrogol™;

DISINTEGRATORS

Starch, hydroxypropyl starch, sodium carboxymethylcellulose, cross-linked sodium carboxymethylcellulose, calcium carboxy methylcellulose, carboxymethylcellulose and low-substituted hydroxypropylcellulose;

SURFACTANTS

Sodium lauryl sulfate, soybean lecithin, sucrose fatty acid esters and Polysolvate 80™;

LUBRICANTS

Talc, waxes, hydrogenated vegetable oils, sucrose fatty acid esters, magnesium stearate, calcium stearate, aluminum stearate and polyethylene glycol;

FLUIDITY ACCELERATORS

Light silicio acid anhydride, dry aluminum hydroxide gel, synthetic aluminum silicate and magnesium silicate;

The compounds represented in the generic formula (I) may be administered in a dosage form such as a suspension, emulsion, syrup, elixir, etc., which may contain a corrective and/or a colorant. It is desirable that these compositions contain 1–95 wt. % of an active ingredient.

Injections are exemplified as pharmaceutical preparations suitable for parenteral administration. These parenteral formulations may be prepared according to usual methods in the art and, generally, distilled water for injection, physiological saline, an aqueous glucose solution, vegetable oils for injection, sesame oil, peanut oil, soybean oil, corn oil, propylene glycol, polyethylene glycol, etc., can be used as a diluent. In addition, a germicide, a preservative and a stabilizer may be added, if necessary.

Considering the stability of compositions for parenteral administration, they may be filled in vials or the like, frozen and lyophylized by usual methods in the art so as for water therein to be removed, followed by reconstitution of solutions from lyophylized compositions just before their use. In addition, if necessary, isotonic agents, stabilizers, preservatives, soothing agents, etc., may be added appropriately.

An injection preparation, for example, as a salt form, may be dissolved in water for injection or may be prepared in a dosage form suitable for injection, such as a suspension or an emulsion in admixture with a pharmaceutically acceptable oil or liquid. In these cases, germicides such as benzylalcohol, antioxidants such as ascorbic acid, buffers, osmotic pressure modifiers, solution adjuvants, etc., may be added. It is preferable for the injection preparation to contain 0.1–5 wt. % of an active ingredient. This can be used in a dosage form of intravenous, intraarterial, intramuscular or subcutaneous injection.

As a pharmaceutical preparation suitable for topical or rectal administration, ointments and suppositories are exemplified.

According to a conventional method, ointments can be prepared by adding basic vehicles and preferably contains 0.5–30 wt. % of an active ingredient. Suppositories may comprise pharmaceutical carriers known in the art, such as polyethylene glycol, lanolin, cacao fat, fatty acid triglycerides and preferably contains 1–95 wt. % of an active ingredient.

The above pharmaceutical preparations suitable for oral, parenteral, topical or rectal application may be prepared, according to the method known in the art, in order to release an active component rapidly, slowly or retardedly after administration to a patient.

The dose level of the therapeutic agent of the present invention for the treatment of xerostomia varies with dosage form, administration method, purpose for application, and the age, the body weight and disease conditions of a patient and, generally, is preferably in a range from about 1 mg to about 1 g per one adult.

The agent may be administered at once or in several portions. The content of an active ingredient in a pharmaceutical preparation is appropriate determined according to the above dose level.

The therapeutic agent of the present invention for the treatment of xerostomia not caused by Sjogren's syndrome can be administered orally or parenterally. A derivative of spirooxathiolane-quinuclidine as an active ingredient acts on exocrine glands, stimulates the muscarinic $M_3$ receptor and augments secretion of saliva without adverse effects. Accordingly, the agents of the present invention can be used for improving and/or curing dry mouth, specifically, caused by various diseases with organic changes in salivary glands, lesions in salivary glands complicated with systemic diseases, necrosis of salivary gland cells by radiotherapy, HIV infection, hypofunction of secretion caused by aging, affection of various medicines taken and further, mental fatigue or stress due to complex social life situations, and can be used for alleviating the pain in a patient.

The present invention is further described more in detail in the following examples, but the scope of the present invention is not restricted by these examples:

EXAMPLE 1

A simulative action on the secretion of saliva in old rats.

A pharmacological activity test was carried out using 5 male Wister rats of the age 50 weeks old in one group. After rats were anesthetized by 40 mg/kg of sodium pentobarbital, 0, 1, 5 and 25 mg/kg of spirooxathiolane-quinuclidine derivative hydrochroride were administered intravenously. Saliva secreted in mouth was collected on a cotton ball at 10, 30 and 60 minutes after the administration and the amount thereof was weighed. The results are shown in table 1.

TABLE 1

| Animal group | dose level (mg/kg) | No. of animals | the amount of secreted saliva (mg/100 g-body weight/minutes) | | |
|---|---|---|---|---|---|
| | | | 10 min. | 30 min. | 60 min. |
| control group | 0 | 5 | 0 | 1 | 0 |
| administered group | 1 | 5 | 3 | 3 | 1 |
| administered group | 5 | 5 | 7 | 5 | 3 |
| administered group | 25 | 5 | 12 | 9 | 5 |

As a result, administration of the aforementioned a derivative of siproxatiolane-quinuclidine hydrochloride increased the amount of saliva secretion in old rats. Accordingly, it was found that the above agent can prevent and/or cure dry mouth.

EXAMPLE 2

A pharmacological activity test was carried out using 5 male Wister rats in one group. At first, 1 mg of reserpine was orally administered. One hour later, 0, 5 and 25 mg/kg of a derivative of spirooxatiolane-quinuclidine hydrochloride represented by formula [II] was orally administered. At 10, 30 and 60 minutes after the administration, saliva secreted in the mouths of the rats was collected in a cotton ball and the amount thereof was weighed. Saliva secretion in the group treated with neither reserpine or quinuclidine derivative was observed in the same way as that in the other groups. The results are shown in table 2.

TABLE 2

| Animal group | dose level (mg/kg) | No. of animals | the amount of secreted saliva (mg/100 g-body-weight/minutes) | | |
|---|---|---|---|---|---|
| | | | 10 min. | 30 min. | 60 min. |
| non-treated group | 0 | 5 | 1 | 2 | 2 |
| cotrol group | 0 | 5 | 0 | 0 | 1 |
| administered group | 5 | 5 | 4 | 6 | 2 |
| administered group | 25 | 5 | 9 | 5 | 4 |

It is clear from the results that administration of the aforementioned of the spirooxa-thioquinuclidine derivative hydrochloride augmented saliva secretion in rats administered reserpine known of inducing dry mouth as its adverse effect.

EXAMPLE 3

Preparation Example 1

Capsule

Capsules of the following composition containing 100 mg of 2-methylspiro(1,3-oxathiolane-5,3')quinuclidine hydrochloride were prepared according to a usual method in the art:

| | |
|---|---|
| 2-methylspiro(1,3-oxothiolane-5,3')quinuclidine hydrochloride (formula II) | 10 g |
| Low-substituted hydroxypropylcellulose(L-HPC) | 20 g |
| Cross-linked carboxymethylcellulose sodium salt (Cross-linked CMC-Na) | 5 g |
| Magnesium stearate | 2 g |
| Lactose | 63 g |
| | 100 g |

Preparation Example 2

Tablets

Tablets of the following composition containing 100 mg of 2-methylspiro(1,3-oxathiolane-5,3')quinuclidine hydrochloride were prepared according to a usual method in the art:

| | |
|---|---|
| 2-methylspiro(1,3-oxothiolane-5,3')quinuclidine hydrochloride (formula II) | 20 g |
| Low-substituted hydroxypropylcellulose(L-HPC) | 10 g |
| Crystalline cellulose | 15 g |
| Hydroxypropylmethylcellulose(HPMC) | 10 g |
| Magnesium stearate | 1 g |
| Lactose | q.s. |
| | 100 g |

Preparation Example 3

Injections

Injections of the following composition containing 100 mg of 2-methylspiro(1,3-oxathiolane-5,3')quinuclidine hydrochloride according to a usual method in the art:

| | |
|---|---|
| 2-methylspiro(1,3-oxathio-5,3')quinuclidine hydrochloride (formula II) | 1 g |
| Glucose | 10 g |
| Distilled water for injection | q.s |
| | 200 ml |

We claim:

1. A method for the treatment of xerostomia not caused by Sjogren's syndrome comprising administering to an affected individual an effective amount of a therapeutic agent comprising a derivative of spirooxathiolane-quinuclidine or an acid addition salt thereof represented by the following formula (I):

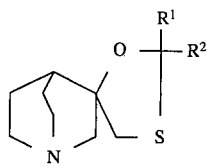

wherein $R^1$ and $R^2$ may be the same or different and each represents hydrogen, alkyl, cyclopentyl, cyclohexyl, aryl, diaryl methylol, or alkyl which may be substituted by one or more aryl groups.

2. A method of treatment of xerostomia according to claim 1 wherein said therapeutic agent comprises 2-methylspiro (1,3-oxathiolane-5,3')-quinuclidine hydrochloride represented by the following formula (II):

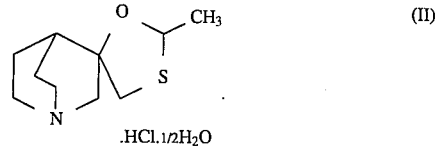

3. A method of treatment for xerostomia according to claim 2 wherein said therapeutic agent comprises the cis-isomer.

* * * * *